United States Patent
Bozzano et al.

(10) Patent No.: US 9,452,956 B1
(45) Date of Patent: Sep. 27, 2016

(54) PROCESSES FOR SEPARATING AN ISOBUTANE RECYCLE STREAM FROM A MIXED C4 STREAM

(71) Applicant: UOP LLC, Des Plaines, IL (US)

(72) Inventors: Andrea G. Bozzano, Northbrook, IL (US); Vesna Havran Mueller, Des Plaines, IL (US); Bing Sun, South Barrington, IL (US); Bipin V. Vora, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/725,681

(22) Filed: May 29, 2015

(51) Int. Cl.
  *C07C 5/25* (2006.01)
  *C07C 41/06* (2006.01)
  *C07C 5/333* (2006.01)
  *C07C 5/03* (2006.01)
  *C07C 2/06* (2006.01)
  *C07C 2/86* (2006.01)

(52) U.S. Cl.
  CPC ............... *C07C 5/3337* (2013.01); *C07C 2/06* (2013.01); *C07C 2/867* (2013.01); *C07C 5/03* (2013.01); *C07C 5/25* (2013.01); *C07C 41/06* (2013.01); *C07C 2523/62* (2013.01)

(58) Field of Classification Search
  None
  See application file for complete search history.

(56) References Cited

U.S. PATENT DOCUMENTS

| | | | |
|---|---|---|---|
| 4,816,607 A | 3/1989 | Vora et al. | |
| 5,338,889 A * | 8/1994 | Vora | ........................ C07C 41/06 568/697 |
| 5,912,191 A | 6/1999 | Nierlich et al. | |
| 6,218,589 B1 | 4/2001 | Cottrell | |
| 6,897,345 B2 | 5/2005 | Marchionna et al. | |
| 8,927,799 B2 | 1/2015 | Myers et al. | |

FOREIGN PATENT DOCUMENTS

EP 2186784 5/2010

* cited by examiner

*Primary Examiner* — Rosalynd Keys

(57) ABSTRACT

Processes for providing an isobutane recycle stream to be recycled to a dehydrogenation zone. In some embodiments a dividing wall column is used to separate a hydrogenation effluent. The hydrogenation effluent may include olefins, or it may be fully saturated. A hydrogenation zone may include a nickel based catalyst and may fully saturate dienes and olefins, or only hydrogenate dienes.

7 Claims, 3 Drawing Sheets

PROCESSES FOR SEPARATING AN ISOBUTANE RECYCLE STREAM FROM A MIXED C4 STREAM

FIELD OF THE INVENTION

This invention relates generally to processes for separating an isobutane recycle stream from a mixed C4 hydrocarbons stream, and more particularly to processes in which the isobutane is recycled back to a dehydrogenation zone.

BACKGROUND OF THE INVENTION

Isobutene can be used to produce a number of desired chemicals. For example, etherification processes make high octane compounds which are used as blending components in lead-free gasoline. These etherification processes will usually produce ethers by combination of an isoolefin with a monohydroxyl alcohol such as methanol or ethanol. The etherification process can also be used as a means to produce pure isoolefins by cracking of the product ether. For instance, pure isobutylene can be obtained for the manufacture of polyisobutylenes and tert-butyl-phenol by cracking methyl tertiary butyl ether (MTBE). The production of MTBE has emerged as a predominant etherification process which uses C4 isoolefins as the feedstock. Apart from the production of MTBE, isobutene can also be used to form other chemicals, including isoprene and isooctane, to name a few.

Typically, a normal butane feed is selectively isomerized to produce isobutane which can be dehydrogenated to form isobutene. However, many dehydrogenation catalysts are particularly sensitive to normal butene. Normal butene can further dehydrogenate forming butadiene which is highly prone to coking, thus normal butenes must be separated from any stream entering the dehydrogenation zone.

Accordingly, most complexes include a fractionation column, such as a deisobutanizer column having about 120 or more distillation trays that is require to separate normal butane and butenes from isobutane. With respect to providing a recycle isobutane feed, the effluent stream produced by the dehydrogenation zone typically contains a low concentration of normal C4 hydrocarbons, due to isomerization activity in the dehydrogenation zone. Therefore, the unconverted C4 hydrocarbons are typically returned to the deisobutanizer column to separate out the normal C4 hydrocarbons.

Furthermore, olefins and dienes in the unconverted stream are typically fully statured to remove any olefins returning to the deisobutanizer column—since normal butene can be harmful for the dehydrogenation zone and olefins can be harmful for the isomerization zone. Typically the saturation zone also requires an oxygenate removal zone to remove any oxygenates from entering the saturation zone to protect the catalyst in the saturation zone.

While these processes are presumable effective for their intended purposes, it is believed that modified process flow schemes may provide for more efficient and economical separation of the isobutane recycle stream.

Moreover, some complexes are provided with a high purity isobutane feed stock, and thus, do not have an isomerization section and a fractionation column. Therefore, the unconverted iC4 hydrocarbons do not have the option to return to the deisobutanizer column. Accordingly, the unconverted iC4 hydrocarbons are typically treated in a raffinate column. However, a raffinate column having about 60 distillation trays typically does not have the ability to separate normal hydrocarbons from iso hydrocarbons as well as a deisobutanizer column can.

Therefore, there remains a need for effective and efficient processes for providing a recycle isobutane feed that does not include normal butane and butenes. It is believed to be desirable in some aspects to eliminate the saturation zone and the required oxygenate removal zone. It is also believed to be desirable in some aspects to optimize fractionation to reduce cost.

SUMMARY OF THE INVENTION

One or more processes have been invented in which an isobutane recycle stream may be provided. In some aspects, the processes allow for the elimination of the oxygenate removal zone from the process. In various aspects, the processes allow for a reduction of the normal hydrocarbons from the iC4 recycle stream with a rerun column (not a deisobutanizer column). In one or more aspects, the processes allow for substitution of the saturation zone catalyst with a nickel based catalyst. Finally in some aspects, the processes allow for consolidation of the depropanizer column with the rerun column into a single column.

In a first embodiment of the invention, the present invention may be characterized broadly as providing a process for converting hydrocarbons by: dehydrogenating isobutane to provide an isobutene rich stream in a dehydrogenation zone; reacting isobutene in a reaction zone to provide a reaction effluent; separating a reaction product from a C4 stream, the C4 stream comprising isobutane, n-butane, 1-butene, 2-butene, and oxygenates; hydrogenating a least a portion of the C4 stream in a hydrogenation zone to provide a hydrogenated effluent, the hydrogenation zone receiving at least a portion of the C4 stream including oxygenates; separating an isobutane recycle stream from the hydrogenated effluent; and, recycling the isobutane recycle stream to the dehydrogenation zone.

In one or more embodiments of the present invention, the process further comprises separating the isobutane recycle stream, a normal paraffin stream comprising normal butane, and a propane stream from the hydrogenated effluent. It is contemplated that the hydrogenated effluent stream is separated in a separation zone having a dividing wall column. It is also contemplated that the hydrogenation zone is configured to hydrogenated both dienes and olefins in the C4 olefin stream. It is further contemplated that the hydrogenation zone is configured to hydrogenate dienes in the C4 olefin stream.

In at least one embodiment of the present invention, the hydrogenation zone includes a nickel based catalyst.

In various embodiments of the present invention, the process further comprises separating a propane stream from the C4 stream before hydrogenating the C4 stream.

In a second embodiment of the present invention, the present invention may be generally characterized as providing a process for converting hydrocarbons by: dehydrogenating isobutane to provide an isobutene rich stream in a dehydrogenation zone; reacting isobutene with methanol to provide an effluent stream, the effluent stream comprising methyl tert-butyl ether; separating a methyl tert-butyl ether product stream from a C4 stream, the C4 stream comprising 1-butene and 2-butene; hydrogenating at least a portion of the C4 stream in a hydrogenation zone to provide a hydrogenated effluent; separating the hydrogenated effluent into an isobutane recycle stream, a normal paraffin stream comprising normal butane, and a propane stream; and, recycling the isobutane recycle stream to the dehydrogenation zone.

In at least one embodiment of the present invention, the process further comprises removing oxygenates from the C4 stream before hydrogenating at least a portion of the C4 stream in the hydrogenation zone.

In some embodiments of the present invention, the hydrogenation zone includes a nickel based catalyst. It is contemplated that the process further comprises injecting sulfur into the hydrogenation zone to selectively hydrogenated dienes in the C4 stream. It is contemplated that the process also comprises selectively isomerizing 1-butene to 2-butene in the hydrogenation zone. It is further contemplated that a conversion ratio of 2-butene to 1-butene is at least 8:1. It is also contemplated that a conversion ratio of 2-butene to 1-butene is at least 12:1. It is even further contemplated that the hydrogenation zone is configured to hydrogenate both dienes and olefins in the C4 stream.

In a third embodiment of the present invention, the present invention may be broadly characterized as providing a process for converting hydrocarbons by: dehydrogenating isobutane to provide an isobutene rich stream in a dehydrogenation zone; reacting isobutene in a reaction zone with formaldehyde to provide an effluent stream, the effluent stream comprising isoprene; separating an isoprene product stream from a C4 stream, the C4 stream comprising 1-butene and 2-butene; separating a propane stream from the C4 stream to provide a depropanized C4 stream, the depropanized C4 olefin stream including oxygenates; hydrogenating the depropanized C4 olefin stream in a hydrogenation zone to provide a hydrogenated effluent; separating the hydrogenated effluent into at least an isobutane recycle stream; and, recycling the isobutane recycle stream to the dehydrogenation zone.

In at least one embodiment of the present invention, the hydrogenation zone includes a nickel based catalyst. It is contemplated that the process includes injecting sulfur into the hydrogenation zone to selectively hydrogenated dienes in the C4 stream. It is also contemplated that the process includes selectively isomerizing 1-butene to 2-butene in the hydrogenation zone. It is further contemplated that the hydrogenation zone is configured to hydrogenate both dienes and olefins in the C4 stream.

Additional aspects, embodiments, and details of the invention, all of which may be combinable in any manner, are set forth in the following detailed description of the invention.

DETAILED DESCRIPTION OF THE DRAWINGS

One or more exemplary embodiments of the present invention will be described below in conjunction with the following drawing figures, in which.

DETAILED DESCRIPTION OF THE INVENTION

As mentioned above, various processes have been invented which allow for an economical process to provide an isobutane recycle stream. The processes may be incorporated into processes which produce isobutene and include an isomerization zone and an deisobutanizer column or into processes which receive a relatively pure isobutene stream and which do not have an isomerization zone and an deisobutanizer column. As mentioned above, some of the processes according to the present invention, utilize a nickel based catalyst in a hydrogenation zone and do not require an oxygenate removal zone from the process. Some processes according to the present invention, allow for a reduction of the normal hydrocarbons from the iC4 recycle stream with a rerun column (not a deisobutanizer column). Furthermore, some processes according to the present invention consolidate a depropanizer column with a rerun column. These processes allow for an efficient and economical separation of an isobutane recycle stream.

With these general principles in mind, one or more embodiments of the present invention will be described with the understanding that the following description is not intended to be limiting.

Figure 1:
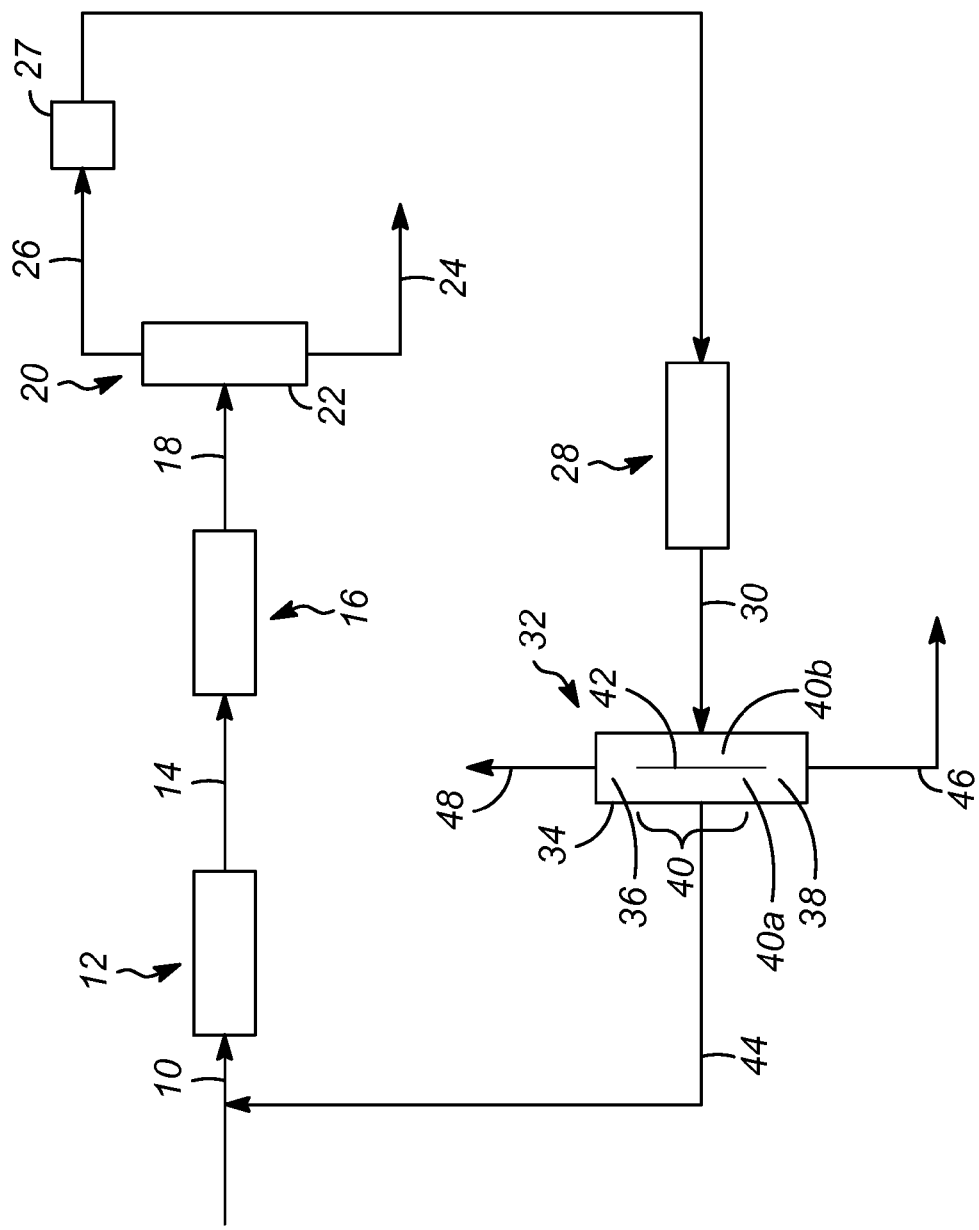
FIG. 1 shows a process flow scheme of one or more embodiments of the present invention.
Figure 2:
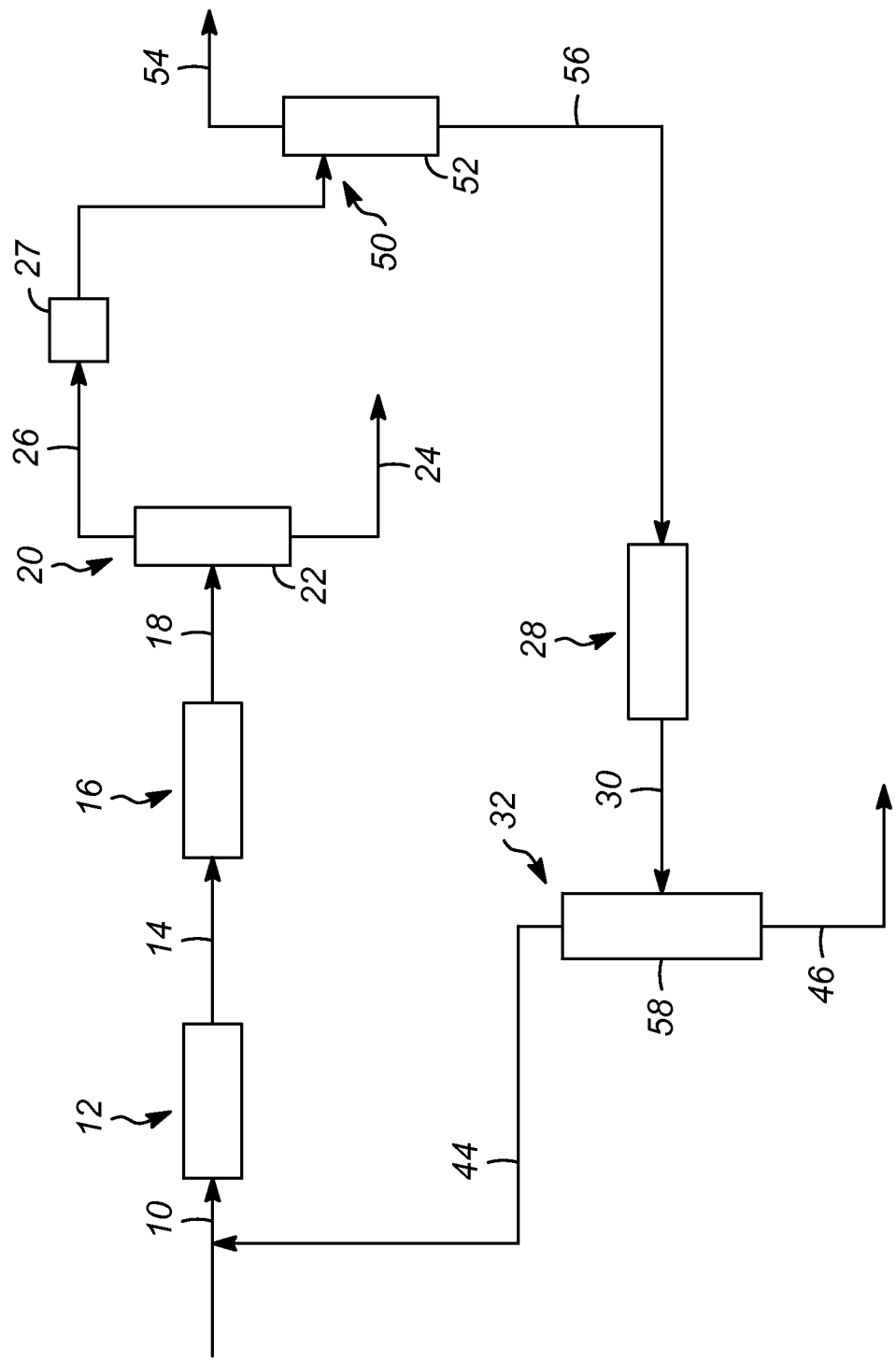
FIG. 2 shows another process flow scheme of various embodiments of the present invention; and, FIG. 3 shows yet another process flow scheme of additional embodiments of the present invention.
Figure 3:
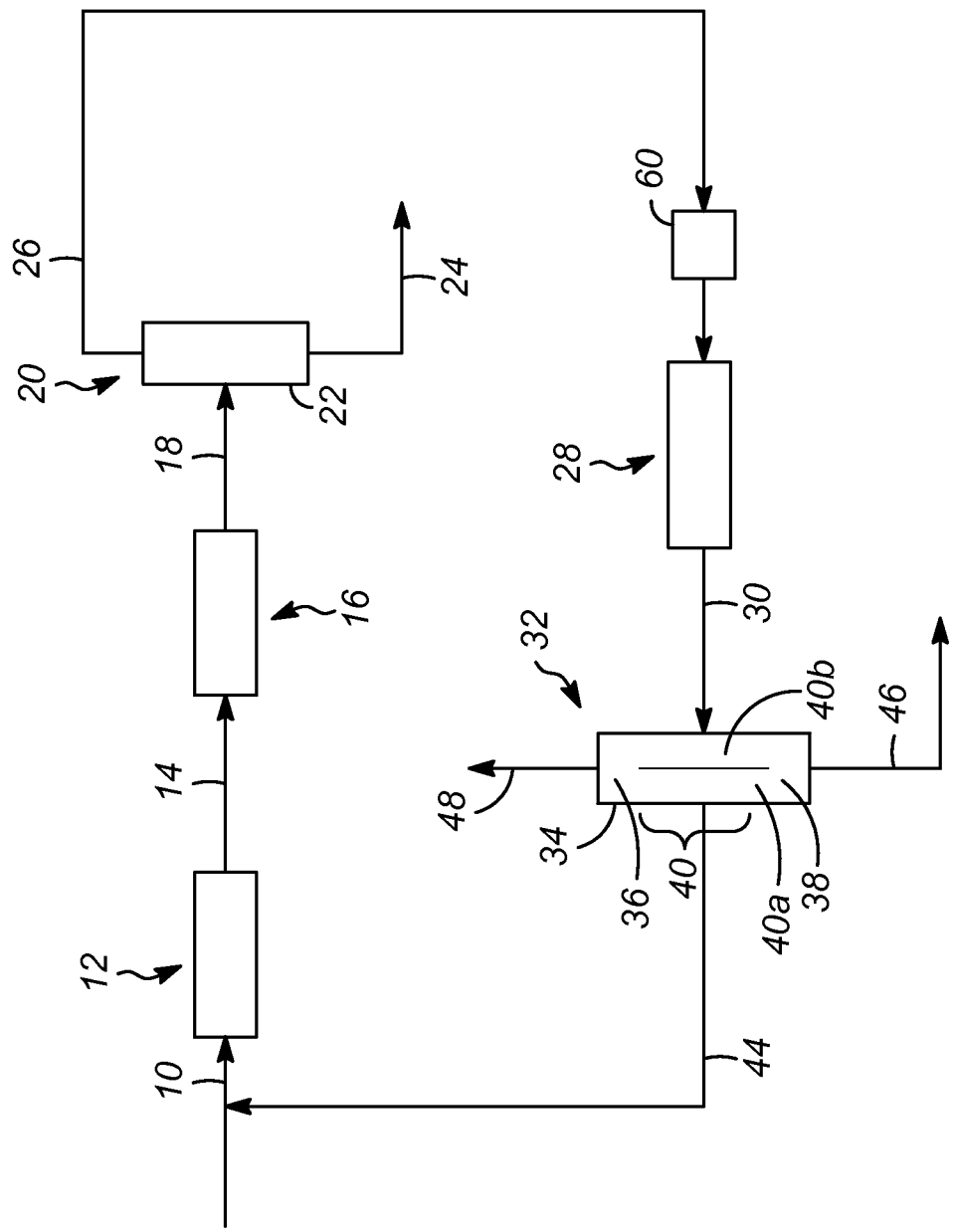

As shown in FIGS. 1 to 3, a feed stream 10 comprising mostly isobutane is passed to a dehydrogenation zone 12. In the dehydrogenation zone 12, the isobutane from the feed stream 10 will be selectively dehydrogenated to form isobutene. Although not depicted as such, the dehydrogenation zone 12 will typically contain a reaction zone and associated auxiliary process equipment such as condensers and a vapor-liquid separator which receives the partially condensed reactor effluent stream. The dehydrogenation zone preferably contains at least one fractionation column. This column is designed and operated to eliminate all lighter boiling components from a net effluent stream from the dehydrogenation zone 12. These lighter boiling compounds may include some and possibly all of the propane, propylene contained in the reactor effluent stream. The propylene may result from the dehydrogenation of a part of propane present in the feed stream to the process or from the cracking of feed butanes. A hydrogen-rich gas stream is separated from the liquid condensed from the reactor effluent. A portion of this gas will normally be recycled and the remainder will be drawn off as a net hydrogen product gas stream. This gas stream will contain a mixture of the various olefins produced in the dehydrogenation zone 12 at a concentration set by the separation conditions.

The dehydrogenation zone 12 preferably comprises at least one radial flow reactor in which the catalyst gradually moves downward by gravity flow to allow the continuous replacement of used catalyst with catalyst having a higher activity. It is preferred that the reactants make at least two passes through a catalyst bed within the reaction zone. A detailed description of moving bed reactors of this type may be obtained by reference to U.S. Pat. Nos. 3,647,680; 3,652,231; 3,706,536; 3,785,963; 3,825,116; 3,839,196; 3,839,197; 3,854,887 and 3,856,662.

The particular dehydrogenation conditions employed within the dehydrogenation zone 12 may vary depending on such factors as the catalyst activity, feed carbon number and the desired conversion. The dehydrogenation zone 12 conditions normally employed for butane dehydrogenation include a temperature of from about 500° to 700° C., a pressure of from 0.5 to about 10 atmospheres absolute and a liquid hourly space velocity of about 1 to 20. The preferred operating temperature will be within the range of from about 550° to about 660° C., and the preferred operating pressure is about 0.5 to 2 atmospheres absolute.

A preferred butane dehydrogenation catalyst is comprised of a platinum group component, a tin component and an alkali metal component with a porous inorganic carrier material. Other catalytic compositions may be used within the dehydrogenation zone 12 if desired. U.S. Pat. No. 4,816,607, the entirety of which is incorporated herein by reference, discloses various characteristics of suitable catalysts.

An isobutene rich stream 14 (meaning that the effluent stream from the dehydrogenation zone 12 has a higher amount of isobutene compared to the feed stream 10 to the dehydrogenation zone 12) may be passed from the dehydrogenation zone 12 to a reaction zone 16.

In the reaction zone 16, the isobutene will be converted into a product in a reaction effluent stream 18. For example, in the reaction zone 16, the isobutene may be subjected to an etherification process and, in the presence of methanol, produce a methyl tert-butyl ether product. Such reaction zones are known in the art. See, U.S. Pat. No. 4,816,607 to Vora, incorporated herein by reference, which discloses a process for the production of methyl tertiary butyl ether and other ethers from precursor light paraffins, olefins and alcohols.

Alternatively, in the reaction zone 16 the isobutene may be subjected to a dimerization process to produce an isooctane product. Such reaction zones are known in the art. See, U.S. Pat. Pub. No. 2015/0045599, incorporated herein by reference.

Additionally, in the reaction zone 16, the isobutene may be reacted with formaldehyde to produce an isoprene product. These reaction zones are likewise known in the art as described in U.S. Pat. No. 3,437,711, U.S. Pat. Pub. No. 2014/0255263, as well as described in "New Synthesis of Isoprene based on Formaldehyde and isobutylene by David W. Hall et al in Ind. Eng. Chem. Prod. Res. Develop., Vol 9 No. 2, 1970" incorporated herein by reference. The particular reaction zone 16 is not necessary for an understanding or practicing of the present invention.

Returning to FIGS. 1 to 3, from the reaction zone 16, the reaction effluent stream 18 comprising the reaction product of the isobutene reaction, as well as other compounds, including, isobutane, n-butane, 1-butene, 2-butene, and oxygenates, is passed to a separation zone 20, preferably including a separation column 22 configured to separate a product stream 24 being rich in the reaction product and a C4 stream 26. The C4 stream 26 may be passed through a water wash 27 to remove some of the oxygenates, like aldehydes, ethers, and alcohols.

With reference to FIG. 1, in some embodiments of the present invention, the C4 stream 26 is passed to a hydrogenation zone 28 which is operated to hydrogenated at least a portion of the C4 stream 26 to provide a hydrogenated effluent 30. The hydrogenation zone 28, in this embodiment preferably, includes a nickel based catalyst which is not as sensitive to water and oxygenates, and thus, allows the process to be practiced without the need for an oxygenate removal zone. However, as discussed below, an oxygenate removal zone may be included in some embodiments. The conditions for the hydrogenation zone 28 are known and a broad range of hydrogenation conditions includes an LHSV (liquid hourly space velocity based at 15° C. liquid) between about 0.5 and 20, a pressure between 5 and 500 psig, and a temperature of 50 to 500° C.

In some embodiments of the present invention, the catalyst in the hydrogenation zone 28 may be sulfided, and the hydrogenation zone 28 may be operated as a selective hydrogenation zone in which the dienes are selectively hydrogenated, but olefins are not hydrogenated. In such an embodiment, the hydrogenation zone 28 will also act to isomerize 1-butene in the C4 stream 26 into 2-buntenes. A ratio of 2-butenes to 1 butene in the hydrogenation zone 28 may be from 8:1 to 12:1. The conversion of some of the 1-butene to 2-butene will allow for easier separation (i.e., less energy and/or shorter separation column) of the isobutane (and possibly isobutene) from the 1-butene, which is discussed below.

In some embodiments, the catalyst in the hydrogenation zone 28 may not be sulfide. In such cases, the hydrogenation zone 28 may be operated to fully hydrogenate all of the olefins and dienes in the C4 stream 26.

In either mode of operation, whether the hydrogenation zone 28 is operated and configured to selectively hydrogenate or to fully saturate, the hydrogenated effluent 30 may be passed to a separation zone 32 having a dividing wall column 34. The dividing wall column 34 comprises a fractionation column in which an upper portion 36 and a lower portion 38 of the column 34 are open, while a middle portion 40 of the column is separated into two portions 40a, 40b by a vertical wall or baffle 42. Such dividing wall column 34 are known in the art.

The dividing wall column 34 will separate the hydrogenated effluent 30 into an isobutane recycle stream 44, a normal paraffin stream 46 comprising normal butane, and a propane stream 48 comprising propane and lighter compounds, such as hydrogen. If the hydrogenation zone 28 is operated to only hydrogenate the dienes in the C4 stream 24, the isobutane recycle stream 44 may also include a small amount of isobutene—which is not harmful to the catalyst in the dehydrogenation zone 12. The isobutane recycle stream 44, along with any isobutene, may be recycled back to the dehydrogenation zone 12 by, for example, being combined with the feed stream 10. The propane stream 48 and the normal paraffin stream 46 may be processed further as is known in the art. The particular processing of these streams is not necessary for the understanding of the present invention.

Turning to FIG. 2, in this embodiment of the present invention, the C4 stream 26 from the separation column 22 (and after the optional water wash 27), is passed to a separation zone 50 including a depropanizer column 52. In the depropanizer column 52, an overhead stream 54 comprising propane may be removed from a bottoms stream 56 rich in C4 hydrocarbons. The overhead stream 54 may be processed in known methods.

The bottoms stream 56 from the depropanizer column 52 may be passed to the hydrogenation zone 28, which may be operated either to fully saturate both olefins and dienes or may be operated to saturate only the dienes and convert 1-butene to 2-butenes, as discussed above. Preferably, as also discussed above, the hydrogenation zone 28 includes a catalyst which comprises a nickel catalyst that is not sensitive to oxygenates, allowing for the process to be practiced without an oxygenate removal zone. Again, however, in some embodiments, an oxygenate removal zone may be included.

The hydrogenated effluent 30 from the hydrogenation zone 28 is passed to the separation zone 32 which includes a rerun column 58 to separate the isobutane recycle stream 44 and the normal paraffin stream 46 comprising normal butane. Any excess hydrogen present in stream 30 will also be recycled to the dehydrogenation zone along with the isobutane.

The isobutane recycle stream 44 may be recycled back to the dehydrogenation zone 12 from the rerun column 58. The remaining portions of this embodiment may be the same as discussed above, therefore, those portions of the above embodiments are expressly incorporated herein by reference.

Turning to FIG. 3, in various embodiments of the present invention, an oxygenate removal zone 60 is disposed upstream of the hydrogenation zone 28. The oxygenate removal zone 60 may comprise any known technology for removing oxygenates from the C4 stream 26. A variety of methods are known to remove such compounds which include water washing, adsorption and extraction processes. Oxygenated compounds and nitrogen compounds can be removed by typical adsorbents for the removal of these contaminants comprised zeolitic molecular sieves. Suitable types of zeolites are faujasites having pore sizes of about 10 angstroms. In particular, such zeolites include X, Y and L types as described in U.S. Pat. Nos. 3,216,789; 2,882,244 and 3,130,007. A particularly preferred type of zeolite is 13X. The use of type 13X sieves for the removal of oxygenate compounds such as dimethyl ethers from the effluent from an etherification process is described in U.S. Pat. No. 4,814,517, the contents of which are hereby incorporated by reference. With the inclusion of the oxygenate removal zone 60, the catalyst in the hydrogenation zone 28 may comprise a noble metal catalyst, such as palladium or other metals typically sensitive to water. Typically, such hydrogenation zones 28 will fully saturate the olefins and dienes in the C4 stream 26. Additionally, in FIG. 3, a water was is not depicted, but may be included and disposed between the hydrogenation zone 28 and the separation zone 20.

As shown in FIG. 3, the hydrogenated effluent 30 may be passed from the hydrogenation zone 28 to the separation zone 32 which includes the dividing wall column 34. As with the discussion of FIG. 1, above, the dividing wall column 34 will provide the isobutane recycle stream 44, the normal paraffin stream 46 comprising normal butane, and the propane stream 48. As in the previously discussed embodiments, the isobutane recycle stream 44 may be passed back to the dehydrogenation zone 12. The remaining portions of these embodiments are similar to the above described embodiments.

In any of the above described embodiments, the isobutane recycle stream may be passed back to the dehydrogenation zone without passing to a deisobutanizer column (to separate out normal butane) and/or an isomerization zone configured to convert normal butanes to isobutane before being passed to the dehydrogenation zone. As mentioned above, some complexes may already receive a high purity isobutane stream and thus may not have such processing capabilities. Furthermore, in some embodiments in which a catalyst that is not sensitive to oxygenates is utilized in the hydrogenation zone, an oxygenate removal zone may be eliminated from the system. Additionally, operating the hydrogenation zone as a selective hydrogenation will allow for isobutene to be recycled, and may allow for more efficient separation of isobutane (and isobutene) form the normal paraffins and olefins. Finally, the use of the dividing wall column may lower capital expenditures and require less space. Thus the various processes provide for efficient and economical processes to provide an isobutane recycle stream.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understanding the embodiments of the present invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for converting hydrocarbons, the process comprising:
   dehydrogenating isobutane to provide an isobutene rich stream in a dehydrogenation zone;
   reacting isobutene with methanol to provide an effluent stream, the effluent stream comprising methyl tert-butyl ether;
   separating a methyl tert-butyl ether product stream from a C4 stream, the C4 stream comprising 1-butene and 2-butene;
   hydrogenating at least a portion of the C4 stream in a hydrogenation zone to provide a hydrogenated effluent, wherein the hydrogenation zone is operated to fully hydrogenate all olefins and dienes;
   separating the hydrogenated effluent, using a rerun column, into an isobutane recycle stream, a normal paraffin stream comprising normal butane, and a propane stream; and,
   recycling the isobutane recycle stream to the dehydrogenation zone.

2. The process of claim 1 further comprising:
   removing oxygenates from the C4 stream before hydrogenating at least a portion of the C4 stream in the hydrogenation zone.

3. The process of claim 1 wherein the hydrogenation zone includes a nickel based catalyst.

4. The process of claim 3 further comprising:
   injecting sulfur into the hydrogenation zone to selectively hydrogenate dienes in the C4 stream.

5. The process of claim 4 further comprising:
   selectively isomerizing 1-butene to 2-butene in the hydrogenation zone.

6. The process of claim 5 wherein a conversion ratio of 2-butene to 1-butene is at least 8:1.

7. The process of claim 5 wherein a conversion ratio of 2-butene to 1-butene is at least 12:1.

* * * * *